United States Patent
Cui et al.

(10) Patent No.: US 9,676,904 B2
(45) Date of Patent: Jun. 13, 2017

(54) METAL ALKOXIDE COMPLEX, CATALYST COMPOSITION, AND PRODUCTION METHOD OF POLYCAPROLACTONE OR POLYLACTIDE

(75) Inventors: Dongmei Cui, Jilin (CN); Xinli Liu, Jilin (CN); Bo Liu, Jilin (CN); Shihui Li, Jilin (CN); Dongtao Liu, Jilin (CN); Chunji Wu, Jilin (CN)

(73) Assignee: Changchun Institute of Applied Chemistry Chinese Academy of Sciences, Changchun (CN)

( * ) Notice: Subject to any disclaimer, the term of this patent is extended or adjusted under 35 U.S.C. 154(b) by 198 days.

(21) Appl. No.: 14/363,281

(22) PCT Filed: Sep. 11, 2012

(86) PCT No.: PCT/CN2012/081244
§ 371 (c)(1),
(2), (4) Date: Aug. 26, 2014

(87) PCT Pub. No.: WO2013/082956
PCT Pub. Date: Jun. 13, 2013

(65) Prior Publication Data
US 2014/0364580 A1 Dec. 11, 2014

(30) Foreign Application Priority Data

Dec. 8, 2011 (CN) .......................... 2011 1 0406325

(51) Int. Cl.
| C08G 63/82 | (2006.01) |
|---|---|
| C08G 63/84 | (2006.01) |
| C07C 31/28 | (2006.01) |
| C07C 29/70 | (2006.01) |
| C07C 33/22 | (2006.01) |
| C07C 33/24 | (2006.01) |
| C08G 63/83 | (2006.01) |
| C08G 63/85 | (2006.01) |
| C07C 31/30 | (2006.01) |
| B01J 31/02 | (2006.01) |
| C07F 3/04 | (2006.01) |
| C07F 5/06 | (2006.01) |

(52) U.S. Cl.
CPC ........ *C08G 63/823* (2013.01); *B01J 31/0212* (2013.01); *C07C 29/70* (2013.01); *C07C 31/28* (2013.01); *C07C 31/30* (2013.01); *C07C 33/22* (2013.01); *C07C 33/24* (2013.01); *C07F 3/04* (2013.01); *C07F 5/069* (2013.01); *C08G 63/826* (2013.01); *C08G 63/83* (2013.01); *C08G 63/84* (2013.01); *C08G 63/85* (2013.01); *B01J 2231/14* (2013.01); *B01J 2531/22* (2013.01)

(58) Field of Classification Search
CPC .............. B01J 2531/22; B01J 2531/23; B01J 2531/24; B01J 2531/25; B01J 2531/31; C07F 3/00; C07F 3/02; C07F 3/04; C07F 5/06; C08G 63/83
See application file for complete search history.

(56) References Cited

U.S. PATENT DOCUMENTS

| 3,679,723 A * | 7/1972 | Tomomatsu ....... C08G 65/2654 502/152 |
|---|---|---|
| 4,055,634 A * | 10/1977 | Brenner ................... A61K 8/58 424/47 |
| 2006/0079437 A1* | 4/2006 | Kondo .................. B29C 33/722 510/505 |
| 2010/0135937 A1* | 6/2010 | O'Brien .................... A61K 8/02 424/59 |

FOREIGN PATENT DOCUMENTS

| CN | 1323844 | A | 11/2001 | | |
|---|---|---|---|---|---|
| CN | 1814645 | A | 8/2006 | | |
| CN | 102407088 | A | 4/2012 | | |
| CN | 102491874 | A | 6/2012 | | |
| CN | 104003841 | | * 8/2014 | ............. | C07C 29/70 |
| DE | 27 29 196 | A1 | * 1/1978 | ............. | C08F 10/00 |
| JP | 55-84308 | | * 6/1980 | ............ | C08F 299/04 |
| JP | 7330757 | A | 12/1995 | | |
| JP | 2011-111461 | | * 6/2011 | ............. | C08G 63/08 |
| JP | 2011-111461 | A | 6/2011 | | |

OTHER PUBLICATIONS

ISR for PCT/CN2012/081244 Translation, dated Dec. 27, 2012.*
Ayres, D.C.; Chambers, M.R. J. Chem. Soc. B: Physical Org. 1967, 12, 1385-1389.*

(Continued)

*Primary Examiner* — Rip A Lee
(74) *Attorney, Agent, or Firm* — Barry L. Davison; Davis Wright Tremaine LLP

(57) ABSTRACT

The invention provides a metal alkoxide complex of Formula (I), wherein X, M, R1, R2, R3, m, n, y and z are as defined in the Description. The invention also provides a catalyst composition comprising the metal alkoxide complex and a hydroxy-containing compound, wherein the molar ratio of the metal alkoxide complex to the hydroxy-containing compound is 1:0.1-1000. The invention also provides a production method of poly-ε-caprolactone or polylactide, wherein an ε-caprolactone monomer or a lactide monomer is reacted in the presence of the metal alkoxide complex or catalyst composition to obtain poly-ε-caprolactone or polylactide. The metal alkoxide complex and the catalyst composition thereof can be used to catalyze the synthesis of poly-ε-caprolactone or polylactide with a high efficiency. The molecular weight of polycaprolactone or polylactide can be controlled by the molar ratio of the metal alkoxide complex and the hydroxy-containing compound, and is adjustable in the range of 1000-600,000, and wherein the molecular weight distribution is from 1.03 to 1.50.

$$[X_{n-m}M(OCR_1R_2R_3)_m]_y \cdot (\text{organic solvent})_z \quad (I)$$

13 Claims, No Drawings

(56) References Cited

OTHER PUBLICATIONS

Ayres, D.C.; Chambers, M.R. J. Chem. Soc. B: Physical Org. 1967, 12, 1389-1392.*
Susz, B.P.; Cooke, I. Helv. Chim. Acta 1954, 37, 1273-1280.*
Malhotra et al. J. Ind. Chem. Soc. 1985, 62, 494-497.*
Okubo, Masao Bull. Chem. Soc. Jpn. 1975, 48, 1057-1058.*
Ashby, E.C.; Goel, A.B. Inorg. Chem. 1979, 18, 1306-1311.*
Masada, H.; Mikuchi, F.; Doi, Y.; Hayashi, A. Nippon Kagaku Kaishi (Chemical Society of Japan) 1995, 2, 164-166.*
Screttas, C.; Steele, B.R. J. Organomet. Chem. 1986, 317, 137-144.*
Malhotra, K.C.; Kaur, A.J.; Kaur Kalra, J.M. J. Ind. Chem. Soc.. 1985, 62, 494-497.*
Okubo, M. Bull. Chem. Soc. Japan, 1975, 48(3), 1057-1058.*
Masada, H.; Mikuchi, F.; Doi, Y.; Hayashi, A. Bull. Chem. Soc. Japan, 1995, 164-166.*
Kricheldorf, H.R. et al., Poly (lactones). 9. Polymerization Mechanism of Metal Alkoxide Initiated Polymerizations of Lactide and Various Lactones. Macromolecules. 1988, vol. 21, No. 2, pp. 286-293, ISSN 0024-9297, abstract, table VII, example 1, table VII, example 2, and table VIII, example 1.
Zhong, Zhiyuan et al., Calcium Methoxide Initiated Ring-Opening Polymerization of ε-caprolactone and L-lactide. Polymer Bulletin. 2001, vol. 46, No. 1, pp. 51-57, ISSN 0170-0839, abstract, p. 54, lines 24, 31-33,42 and 44, p. 55, lines 7 and 9, table 2.
Zhong, Zhiyuan et al., Fast and Living Ring-Opening Polymerization of L-Lactide Initiated with In-situ-Generated Calcium Alkoxides. Journal of Polymers and the Environment. 2001, vol. 9, No. 1, pp. 31-38, ISSN 1566-2543, abstract, p. 32, paragraph 1, figure 3, and table 1.

* cited by examiner

METAL ALKOXIDE COMPLEX, CATALYST COMPOSITION, AND PRODUCTION METHOD OF POLYCAPROLACTONE OR POLYLACTIDE

CROSS-REFERENCE TO RELATED APPLICATIONS

This application is the United States national phase, under 35 U.S.C. §371, of International Patent Application No. PCT/CN2012/081244, filed 11 Sep. 2012 and entitled METALLIC ALKOXY COMPLEX, CATALYST COMPOSITION AND POLYCAPROLACTONE OR POLYLACTIDE PREPARATION METHOD, which claims the benefit of priority to Chinese Patent Application Serial Number 201110406325.6 filed 8 Dec. 2011 and entitled METALLIC ALKOXY COMPLEX, CATALYST COMPOSTION AND POLYCAPROLACTONE OR POLYLACTIDE PREPARATION METHOD, both of which are incorporated herein by reference in their entirety.

FIELD OF THE INVENTION

The invention relates to the field of catalysts, in particular, to a metal alkoxide complex, a catalyst composition and a production method of polycaprolactone or polylactide.

BACKGROUND OF THE INVENTION

Both of poly-ϵ-caprolactone (PCL) and polylactide (PLA) are biodegradable material of polyesters and have excellent biodegradability, thus they are widely used in producing disposable containers, tableware, thin films, fibers, clothes and automotive elements, which is of benefit to solve the environment pollution problem caused by petroleum chemical resources, Furthermore, PCL and PLA also have properties such as good biocompatibility, nontoxicity and adjustable degradability, thus they meet the requirements of high molecular materials useful in medicine and have a prospect for use in internal/external fixation of fracture, surgical suture, stent in tissue engineering and sustained release of drugs, release-controlling support materials and the like.

The earlier synthesis of polyesters is mainly the condensation reaction of acids and alcohols. However, the polymer structure synthesized by such reaction cannot be controlled, and possibly is a linear, branched or cyclic structure, and the molecular weight distribution thereof is too wide, the molecular weight thereof is low and is hard to be controlled, so that the mechanic properties of the polymer are poor eventually. In recent years, researches on the synthesis of polyesters are mainly focused on developing the coordination polymerization catalyst to initiate the ring opening of cyclic esters to produce polyester polymers. Compared with the direct dehydration polycondensation method, the ring opening polymerization method for producing polyesters has the following method, the ring opening polymerization method for producing polyesters has the following advantages: (1) the molecular weight of polyesters can be controlled precisely, and the molecular weight distribution is very narrow; (2) the polyesters obtained by the direct dehydration condensation have a low molecular weight and the properties thereof cannot satisfy certain requirements in biomedicine, while no any water is produces in the ring opening polymerization and thus polymers having a higher molecular weight can be synthesized; (3) selective polymerization of chiral monomers can be achieved by modifications on the catalyst ligands.

The catalyst systems applied in the coordination ring opening polymerization of lactones mainly include stannous octoate, the complexes of aluminum, calcium, magnesium, zinc and titanium, the complexes of metals of group IIIB, and the like. For example, the Chinese patent document with the application number 01114244.8 discloses a method for producing poly-ϵ-caprolactone by using stannous octoate as the catalyst. However, the molecular weight of the poly-ϵ-caprolactone obtained by the catalysis with stannous octoate cannot be controlled, and the molecular weight distribution thereof is wide. The Chinese patent document with the application number 200610016623.3 discloses a production method and use method of a Schiff base aluminum catalyst for the ring opening polymerization of lactide. However, the catalytic activity of the Schiff base aluminum is low, and the molecular weight of the polylactide obtained eventually is relatively low.

SUMMARY OF THE INVENTION

In view of above, the technical problem sought to be solved by the invention is to provide a metal alkoxide complex having high catalytic activity, and the polycaprolactone or polylactide produced by the catalysis thereof has a controllable molecular weight and a narrow molecular weight distribution, a catalyst composition thereof, and a production method of polycaprolactone or polylactide using the metal alkoxide complex and the catalyst composition thereof.

The invention provides a metal alkoxide complex having a molecular formula represented by Formula (I):

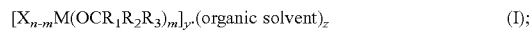

$$[X_{n-m}M(OCR_1R_2R_3)_m]_y \cdot (\text{organic solvent})_z \qquad (I);$$

In the formula (I), M is a main group metal element or a transition metal element in the periodic table;

$R_1$, $R_2$ and $R_3$ are independently selected from hydrogen, chain alkyl, phenyl, substituted phenyl, arylalkyl, or substituted arylalkyl;

X is hydrogen, C1-C30 chain alkyl, amino or halogen;

n is the valence state of M, and n=1–4;

m is the number alkoxy group in the complex, and 0<m≤4;

0≤n−m<4;

1≤y≤6; and

0≤z≤4.

Preferably, said M is calcium, magnesium, strontium, barium, aluminum or zinc.

Preferably, said $R_1$, $R_2$ and $R_3$ are independently selected from C1-C5 chain alkyl, phenyl substituted with C1-C6 chain alkyl or arylalkyl.

Preferably, said X is —CH₃, —CH₂CH₃, —CH₂CH₂CH₂CH₃, —CH₂Si(CH₃)₃, —N(Si(CH₃)₃)₂ or —Cl.

Preferably, said organic solvent is alkanes, substituted alkanes, benzene, substituted benzenes, or ethers.

The invention also provides a catalyst composition comprising the metal alkoxide complex, and hydroxy-containing compound, wherein the molar ration of said metal alkoxide complex to said hydroxy-containing compound is 1:0.1-1000.

Preferably, said hydroxy-containing compound is methanol, ethanol, n-propanol, iso-propanol, n-butanol, iso-butanol, ethylene glycol, phenol, benzoic alcohol, phenethanol, diphenylcarbinol, triphenylcarbinol, 1,1,1-triphenylethanol, 9-antracenemethanol, 1,3,5-benzenetriol, triethanolamine or 1,3,5-benzenetrimethanol.

The invention also provides a production method of poly-ε-caprolactone or polylactide comprising the following step:

a ε-caprolactone monomer or a lactide monomer is reacted in the presence of a catalyst to obtain poly-ε-caprolactone or polylactide, wherein the catalyst is said metal alkoxide complex or said catalyst composition.

Preferably, the molar ration of said metal alkoxide complex to said ε-caprolactone monomer or lactide monomer is 1:1-10000.

Preferably, the reaction temperature is 10° C.-130° C., and the reaction time is 0.03 h-24 h.

The metal alkoxide complex provided by the invention has a molecular formula represented by Formula (I), said metal alkoxide complex alone can be used as the catalyst for catalyzing the polymerization of ε-caprolactone monomer or lactide monomer. Furthermore, its catalytic activity is high, and the polycaprolactone or polyactide having a high molecular weight can be obtained eventually. The invention also provides a catalyst composition comprising said metal alkoxide complex and a hydroxy-containing compound, the combination use of they both improves the catalytic efficiency of the metal alkoxide complex, and the polycaprolactone or polylactide having a high molecular weight can be obtained by the catalysis with an extremely small amount of metal alkoxide complex, namely the catalytic efficiency is very high. At the same time, during the catalysis, a living chain transfer is occurred in the hydroxy-containing compound and the initiating center, thereby the chain of polycaprolactone or polylactide is continuously extended, showing an "immortal" polymerization property and the molecular weight distribution being close to 1. Thus, the molecular weight of the poly-ε-caprolactone or polylactide can be controlled either by the molar ratio of monomer as the raw material to the metal alkoxide complex or by the molar ration of monomers as the raw material to the hydroxy-containing compound, so that the molecular weight of the poly-ε-caprolactone or polylactide is adjustable in the range of 1000-600,000, and the molecular weight distribution is preferably from 1.03 to 1.50.

DETAILED DESCRIPTION OF THE INVENTION

The invention provides a metal alkoxide complex having a molecular formula represented by Formula (I):

$$[X_{n-m}M(OCR_1R_2R_3)_m]_y \cdot (\text{organic solvent})_z \quad (I)$$

in Formula (I), M is a main group metal element or a transition metal element in the periodic table;

$R_1$, $R_2$ and $R_3$ are independently selected from hydrogen, chain alkyl, phenyl, substituted phenyl, arylalkyl, or substituted arylalkyl;

X is hydrogen, C1-C30 chain alkyl, amino or halogen;

n is the valence state of M, and n=1-4;

m is the number of alkoxy group in the complex, and $0 < m \leq 4$;

$0 \leq n-m < 4$;

$1 \leq y \leq 6$; and $0 \leq z \leq 4$.

In Formula (I), said M is a main group metal element or a transition metal element in the periodic table, preferably calcium, magnesium, strontium, barium, aluminum or zinc, more preferably calcium, magnesium or zinc, n is the valence state of M, and depending on the metal element used, n can be 1, 2, 3 or 4, preferably 2 or 3; m is the number of alkoxy group in the complex, and $0 < m \leq 4$. As the metal-alkoxy bond is the initiating group of said metal alkoxide complex, at least one metal-alkoxy bond is contained, and thus n and m need to satisfy n−m≥0, m can be 0 or 1; and when n is 3 or more, m also can be 2 or more.

Said $R_1$, $R_2$ and $R_3$ are independently selected from hydrogen, chain alkyl, phenyl, substituted phenyl, arylalkyl, or substituted arylalkyl; said chain alkyl is preferably C1-C20 chain alkyl, more preferably C1-C15 chain alkyl, and most preferably C1-C5 chain alkyl; said substituted phenyl is preferably phenyl substituted with C1-C20 chain alkyl, more preferably phenyl substituted with C1-C15 chain alkyl, and most preferably phenyl substituted with C1-C6 chain alkyl. In the invention, said $R_1$, $R_2$ and $R_3$ are most preferably hydrogen, methyl or phenyl, substituted phenyl, arylalkyl, substituted arylalkyl, respectively.

Said X is an atom or group forming a bond with M, and X is hydrogen, C1-C30 chain alkyl, amino or halogen, preferably hydrogen, $CH_3$, $CH_2CH_3$, $CH_2CH_2CH_2CH_3$, $CH_2Si(CH_3)_3$, $N(Si(CH_3)_3)_2$, F, Cl, Br, or I, and more preferably $CH_3$, $CH_2CH_3$, $CH_2CH_2CH_2CH_3$, $CH_2Si(CH_3)_3$, $N(Si(CH_3)_3)_2$ or Cl.

Said organic solvent is preferably alkanes, substituted alkanes, benzene, substituted benzene, or ethers, more preferably pentane, hexane, benzene, chlorobenzene, o-dicholorbenzene, toluene, ethyl ehter, tetrahydrofuran, ethylene glycol dimethyl ether, dichloromethane or dioxane, and most preferably toluene, tetrahydrofuran or dichloromethane. Said organic solvent is chelated to metals via oxygen atom, thus when said organic solvent is a non-polar solvent, said z satisfies z=0; and when said organic solvent is a polar solvent, said z satisfies $0 \leq z \leq 4$.

In the invention, $R_1$, $R_2$ and $R_3$ are independently selected from hydrogen, chain alkyl, phenyl, substituted phenyl, arylalkyl, substituted arylalkyl; and when the steric hindrance constituted by the three groups is large enough, y=1, or when the steric hindrance is relatively small, $1 < y \leq 6$.

Said metal alkoxide complex can be produced by the following method.

A metal compound $MX_n$ and a ligand $R_1R_2R_3COH$ are dissolved in an organic solvent, and are reacted under the catalysis of a catalyst to obtain a mixture; the mixture is washed and filtered to obtain said metal alkoxide complex, and the specific reaction is as follows.

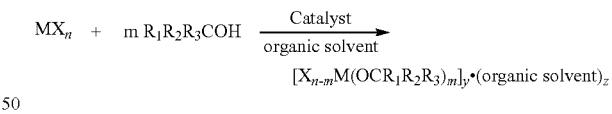

$MX_n$ is a metal compound, wherein M is a main group metal element or a transition metal element in the periodic table, preferably calcium, magnesium, strontium, barium, aluminum or zinc, and more preferably calcium, magensium or zinc; said X is hydrogen, C1-C30 chain alkyl, amino or halogen, preferably hydrogen, $CH_3$, $CH_2CH_3$, $CH_2CH_2CH_2CH_3$, $CH_2Si(CH_3)_3$, $N(Si(CH_3)_3)_2$, F, Cl, Br or I, and more preferably $CH_3$, $CH_2CH_3$, $CH_2CH_2CH_2CH_3$, $CH_2Si(CH_3)_3$, $N(Si(CH_3)_3)_2$ or Cl; n is the valence state of M, and depending on the metal element adopted, n can be 1, 2, 3 or 4, and preferably 2 or 3; m is the number of alkoxy group in the complex, and $0 \leq m \leq 4$. As the metal-alkoxy bond is the initiating group of said metal alkoxide complex, at least one metal-alkoxy bond is contained, and thus n and m need to satisfy n−m≥0, m can be 0 or 1, and when n is 3 or more, m also can be 2 or more. When the organic solvent is a non-polar solvent, said z satisfies z=0; and when the organic solvent is polar solvent, said z satisfies z=0-4. $R_1$, $R_2$ and $R_3$ are independently selected from hydrogen, chain alkyl, phenyl, substituted phenyl, arylalkyl, substituted arylalkyl. When the steric hindrance constituted by the three groups is large enough, y=1, or when the steric hindrance is relatively small, 1<y≤6.

$R_1R_2R_3COH$ is the ligand, wherein $R_1$, $R_2$ and $R_3$ are independently selected from hydrogen, chain alkyl, phenyl, substituted phenyl, arylalkyl, or substituted arylalkyl. Said chain alkyl is preferably C1-C20 chain alkyl, more preferably C1-C15 chain alkyl, and most preferably C1-C5 chain alkyl. Said substituted phenyl is preferably phenyl substituted with C1-C20 chain alkyl, more preferably phenyl substituted with C1-C15 chain alkyl, and most preferably phenyl substituted with C1-C6 chain alkyl. In the invention, said $R_1$, $R_2$ and $R_3$ are most preferably hydrogen, methyl or phenyl, respectively:

In the method for producing said metal alkoxide complex, said organic solvent is alkanes, substituted alkanes, benzene, substituted benzene or ethers, preferably pentane, hexane, benzene, chlorobenzene, o-dichlorobenzene, toluene, ethyl ether, tetrahydrofuran, ethylene glycol dimethyl ether, dichloromethane or dioxane, and more preferably toluene, tetrahydrofuran or dichloromethane.

In the method for producing said metal alkoxide complex, said catalyst is preferably elementary iodine. The amount of catalyst added is preferably 2%-5% of the total mass of the reactants.

In the method for producing said metal alkoxide complex, as the metal alkoxide complex is sensitive to oxygen and water, said reaction is preferably performed by adding the ligand-containing organic solvent to the solution of the metal compound $MX_n$ in the organic solvent slowly and dropwisely under water-free and oxygen-free condition with a rapid agitation.

In the method for producing said metal alkoxide complex, said reaction is preferably performed under a reflux condition, so that the reaction temperature is maintained and the conversion measured by nuclear magnetic resonance test of the reaction is improved. The reaction time is preferably 1-4 h, and more preferably 2-3 h. The reaction temperature is not specifically limited, and is preferably at room temperature.

The initiating site of said metal alkoxide complex is the metal-alkoxy bond. This initiating group has a very high catalytic efficiency for polar cyclic esters monomers, which can reach 100000% (i.e. 1000 times), thereby said metal alkoxide complex exhibits a relatively high catalytic activity on the polymerization of ε-caprolactone and lactide monomers. Therefore, said metal alkoxide complex can catalyze the polymerization of ε-caprolactone and lactide monomers to produce polymers.

The invention also provides a catalyst composition comprising the above-mentioned metal alkoxide complex and a hydroxy-containing compound, wherein the molar ratio of the metal alkoxide complex to the hydroxy-containing compound is 1:0.1-1000, preferably 1:100-900, and more preferably 1:300-700.

Said hydroxy-containing compound can be represented by Formula (II):

R(OH)$_w$ (II).

In Formula (II), R is C1-C20 chain alkyl, C1-C20 chain alkyl substituted by amino, aryl, arylalkyl, aryl or arylalkyl substituted by C1-C20 chain alkyl; and w is a natural number, preferably 1≤w≤8.

Said hydroxy-containing compound can be alcohols, and also can be phenols. It is preferably methanol, ethanol, n-propanol, iso-propanol, n-butanol, iso-butanol, ethylene glycol, phenol, benzoic alcohol, phenethanol, diphenylcarbinol, triphenylcarbinol, 1,1,1-triphenylethanol, 9-anthracenemethanol, 1,3,5-benzentriol, triethanolamine or 1,3,5-benzenetrimethanol, more preferably isopropanol, benzoic alcohol, diphenycarbinol or triphenylcarbinol.

The initiating site of said metal alkoxide complex is the metal-alkoxy bond. This initiating site is characterized by exhibiting a high efficiency and a high activity for polar cyclic esters monomer, thereby said metal alkoxide complex exhibits a relatively high catalytic activity for ε-caprolactone or lactide monomers. Said metal alkoxide complex can be used alone to catalyze polymers, or, can be used in combination with the hydroxy-containing compound to catalyze ε-caprolactone and lactide monomers to produce polymers.

When a conventional catalyst is used to catalyze the polymerization of monomers, the addition of alcohols often results in deactiviation of the catalyst, so that the chain propagation reaction of the polymer is terminated. However, the inventor has discovered that, in the invention, when a hydroxy-containing compound is added, said metal alkoxide complex can still catalyze the chain propagation reaction of the polymer as usual without causing the polymerization to be terminated. When said catalyst composition is used to catalyze the polymerization of ε-caprolactone or lactide monomers, and the hydroxy-containing compound plays the role of a chain-transfer agent, namely the hydroxy-containing compound and the initiating center can occur the living chain transfer, so that the chain of the polymer can be continuously propagated, the apparent effect thereof is that one metal alkoxide complex molecule can initiate 1-1000 times chain propagation of the macro molecular, so the catalytic efficiency can be up to 100,000%, showing an "immortal" polymerization nature. With this nature, the adjustment of the molecular weight of the polymer in a very wide range can be achieved by controlling the addition amount of the hydroxy-containing compound. At the same time, the addition of the hydroxy-containing compound also results in an ideal molecular weight distribution of the polymer.

The two components of the catalyst composition of the invention can be added separately during the reaction, but they also can be added simultaneously after the treatment according to the following method:

adding the organic solvent containing said metal alkoxide complex to the organic solvent containing the hydroxy-containing compound slowly and dropwise under a dry condition with rapid agitation, and vacuum filtering the resultant mixture to obtain the catalyst composition, wherein the organic solvent containing said metal alkoxide complex and the organic solvent containing the hydroxy-containing compound can be same or different, preferably they both are same, and each of them is independently selected from alkanes, substituted alkanes, benzene, substituted benzene or ethers, preferably pentane, hexane, benzene, chlorobenzene, o-dichlorobenzene, toluene, ethyl ether, tetrahydrofuran, ethylene glycol dimethyl ether, dichloromethane or dioxane, and more preferably toluene, tetrahydrofuran or dichloromethane.

The invention also provides a production method of poly-ε-caprolactone and polylactide comprising the following steps:

ε-caprolactone monomers or lactide monomers are reacted in the presence of a catalyst to obtain poly-ε-caprolactone or polylactide, wherein the catalyst is said metal alkoxide complex, or said catalyst composition consisted of the metal alkoxide complex and hydroxy-containing compound.

In said catalyst, the molar ratio of the metal alkoxide complex to the ε-caprolactone monomer or lactide monomer is 1:1-10,000, and preferably 1:1000-9,000.

The polymerization reaction time of the ε-caprolactone monomers or lactide monomers is preferably 0.03 h-24 h, more preferably 0.5 h-20 h, and most preferably 3 h-10 h. The polymerization reaction temperature of the ε-caprolactone monomers or lactide monomers is preferably 10° C.-130° C., and more preferably 25° C.-100° C.

As the metal alkoxide complex is sensitive to oxygen and water, said reaction is preferably performed under a water-free and oxygen-free condition. For example, the reaction of the ε-caprolactone monomers or lactide monomers can be catalyzed by said catalyst directly, or the reaction of the ε-caprolactone monomers or lactide monomers can be catalyzed by said catalyst catalyzes in an organic solvent, wherein the organic solvent is alkanes, substituted alkanes, benzene, substituted benzene or ethers, preferably pentane, hexane, benzene, chlorobenzene, o-dichlorobenzene, toluene, ethyl ether, tetrahydrofuran, ethylene glycol dimethyl ether, dichloromethane or dioxane, and more preferably toluene, tetrahydrofuran or dichloromethane.

After the reaction is completed, poly-ε-caprolactone or polylactide is obtained by a post-treatment, which comprises adding the mixed liquid from the reaction to the protic solvent, such as a solution 10 voL % hydrochloric acid in alcohol (e.g. ethanol), to stop the reaction; then performing sedimentation in ethanol, and a white solid is obtained by filtration; drying the white solid at 30° C.-50° C. for 36 h-60 h to obtain poly-ε-caprolactone or polylactide.

The molecular weight of the poly-ε caprolactone or polylactide is measured by a gel permeation chromatography (GPC). The results shows that the molecular weight of the poly-ε-caprolactone or polylactide can be adjusted by means of the molar ratio of monomers of the raw material to the metal alkoxide complex, or by means of the molar ratio of monomer as the raw material to the hydroxy-containing compound, and the molecular weight of the poly-ε-caprolactone or polylactide is adjustable in the range of 1000-600,000, wherein the molecular weight distribution is from 1.03 to 1.50.

The invention provides a metal alkoxide complex and a catalyst composition consisting of said metal alkoxide complex and a hydroxy-containing compound. Said metal alkoxide complex can be used as a catalyst alone, or can be used as a catalyst in the form of a catalyst composition. When said catalyst composition is used to catalyze the polymerization of ε-caprolactone and lactide monomers, polycaprolactone or polylactide having a high molecular weight can be obtained by the catalysis with an extremely small amount of the metal alkoxide complex, namely the catalytic efficiency is very high. At the same time, during the catalysis, the hydroxy-containing compound and the initiating center can occur a living chain transfer, thereby the chain of polycaprolactone or polylactide can be continuously extended, showing an "immortal" polymerization nature, and the molecular weight distribution is close to 1.

In order to further understand the invention, the metal alkoxide complex, the catalyst composition, and the production method of polycaprolactone or polylactide of the invention will be described in detail in combination with Examples. The protection scope of the invention is not limited by these Examples.

EXAMPLES

Example 1

Production of Metal Alkoxide Complexes A1-A6

Under a water-free and oxygen-free condition, 10 mL of a toluene solution containing benzoic alcohol was added to a toluene solution containing calcium chloride slowly and dropwise, wherein the content of the benzoic alcohol was 0.22 g (2 mmol), and the content of the calcium chloride was 0.11 g (1 mmol). 0.017 g of elementary iodine was added, and the reaction was performed under reflux at 120° C. for 24 h, the reaction equation was as follows:

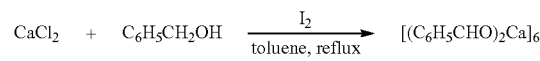

The resultant reaction mixture was cooled, and 0.25 g of the complex A1 was obtained as white solid after filtration with the yield of 76%.

The element analysis of the complex A1 was performed (multi-element analyzer, QL-S3000A, Changchun Institute of Applied Chemistry), and it had the molecular formula of $(C_{14}H_{12}CaO_2)_6$ and the molecular weight of 1513.92: C, 66.64; H, 4.79; Ca, 15.88; O, 12.68.

The production methods of complexes A2-A6 were same with that of the complex A1, except that methanol, ethanol, iso-propanol, n-butanol, t-butanol, and phenol was used as the reactants in this order to react with calcium chloride to obtain complexes A2-A6, respectively.

The element analysis of the resultant complexes A2-A6 was performed.

The complex A2 had the molecular formula of $(C_2H_6CaO_2)_6$ and the molecular weight of 612.9: C, 23.52; H, 5.92; Ca, 39.24; O, 31.33.

The complex A3 had the molecular formula of $(C_4H_{10}CaO_2)_2$ and the molecular weight of 260.4: C, 36.90; H, 7.74; Ca, 30.78; O, 24.58.

The complex A4 had the molecular formula of $(C_6H_{14}CaO_2)_2$ and the molecular weight of 315.5: C, 45.54; H, 8.92; Ca, 25.33; O, 20.22.

The complex A5 had a molecular formula of $(C_8H_{18}CaO_2)_2$ and the molecular weight of 372.62: C, 51.57; H, 9.74; Ca, 21.51; O, 17.18.

The complex A6 had the molecular formula of $C_8H_{18}CaO_2$ and the molecular weight of 186.31: C, 51.57; H, 9.74; Ca, 21.51; O, 17.18.

Example 2

Production of Metal Alkoxide Complexes A7-A9

Under a water-free and oxygen-free condition, 10 mL of a tetrahydrofuran solution containing phenylmethylmethanol was added to a tetrahydrofuran solution containing trimethyl aluminum slowly and dropwise, wherein the content of the phenylmethylmethanol was 0.36 g (3 mmol), and the content of trimethyl aluminum was 0.07 g (1 mmol); the reaction was performed under reflux at 70° C. for 24 h, the reaction equation was as follows:

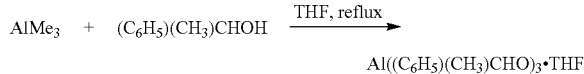

The resultant reaction mixture was cooled and concentrated, and 0.40 g of the complex A7 was obtained as white powder after filtration with the yield of 87%.

The element analysis of the complex A7 was performed, and it had the molecular formula of $(C_{24}H_{27}AlO_3)(THF)$ and the molecular weight of 462.24: C, 72.70; H, 7.63; Al, 5.83; O, 13.84.

The production methods of complexes A8 and A9 were same with that of A7, except that trimethyl aluminum is reacted with t-butanol and phenol, respectively.

The complex A8 had the molecular formula of $(C_{12}H_{27}AlO_3)(THF)$ and the molecular weight of 318.43: C, 60.35; H, 11.08; Al, 8.47; O, 20.10.

The complex A9 had the molecular formula of $(C_{18}H_{15}AlO_3)_2(THF)$ and the molecular weight of 756.8: C, 69.83; H, 6.13; Al, 7.13; O, 16.91.

Example 3

Production of Metal Alkoxide Complexes A10-A14

Under a water-free and oxygen-free condition, 10 mL of a toluene solution containing benzoic alcohol was added to a toluene solution containing bistrimethylsilylamino magnesium slowly and dropwise, wherein the content of the benzoic alcohol was 0.22 g (2 mmol), and the content of the bistrimethylsilylamino magnesium was 0.11 g (1 mmol); then 0.017 g of elementary iodine was added. The reaction was performed under reflux for 24 h, the reaction equation was as follows:

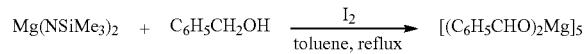

The resultant reaction mixture was cooled, 0.38 g of complex as white solid A10 was obtained after filtration with the yield of 90%.

The element analysis of the complex A10 was performed, and it had the molecular formula of $(C_{14}H_{12}MgO_2)_5$ and the molecular weight of 1182.5: C, 71.08; H, 5.11; Mg, 10.27; O, 13.53.

The production methods of complexes A11-A14 were same with that of A10, except that methanol, t-butanol, and diphenylcarbinol were used as the reactants in this order to react with bistrimethylsilylamino magnesium to obtain complexes A11-A13, respectively.

The element analysis of the resultant complexes A11-A14 was performed. The complex A11 had the molecular formula of $(C_2H_6MgO_2)_6$ and the molecular weight of 518.22: C, 27.81; H, 7.00; Mg, 28.14; O, 37.05;

The complex A12 had the molecular formula of $(C_4H_{10}MgO_2)_6$ and the molecular weight of 686.58: C, 41.99; H, 8.81; Mg, 21.24; O, 27.96;

The complex A13 had the molecular formula of $(C_{12}H_{10}MgO_2)_5$ and the molecular weight of 1052.55: C, 68.47; H, 4.79; Mg, 11.55; O, 15.20;

The complex A14 had the molecular formula of $(C_{26}H_{22}MgO_2)_4$ and the molecular weight of 1563.04: C, 79.92; H, 5.67; Mg, 6.22; O, 8.19.

Example 4

Production of Metal Alkoxide Complex A15

Under a water-free and oxygen-free condition, 10 mL of a tetrahydrofuran solution containing t-butanol was added to a tetrahydrofuran solution containing iron chloride slowly and dropwise, wherein the content of the t-butanol was 0.23 g (3 mmol), and the content of the tetrahydrofuran solution of the iron chloride was 0.13 g (1 mmol), and then 0.020 g elementary iodine was added. The reaction was performed under reflux for 24 h, the reaction equation was as follows:

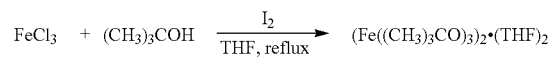

The resultant reaction mixture was cooled, and 0.40 g of the complex A19 was obtained as white solid after filtration with the yield of 82%.

The element analysis of the complex A15 was performed, and it had the molecular formula of $C_{20}H_{43}FeO_5$ and the molecular weight of 838.5: C, 57.28; H, 10.33; Fe, 13.32; O, 19.07.

Example 5

Production of Metal Alkoxide Complexes A16-A19

Under a water-free and oxygen-free condition, 10 mL of a toluene solution containing benzoic alcohol was added to a toluene solution containing diethyl zinc slowly and dropwise, wherein the content of the benzoic alcohol was 0.37 g (2 mmol), and the content of the diethyl zinc was 0.12 g (1 mmol), and then 0.025 g of elementary iodine was added. The reaction was performed under reflux for 24 h, the reaction equation was as follows:

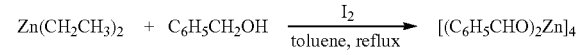

The resultant reaction mixture was cooled, and 0.40 g of the complex A16 was obtained as white solid after filtration with the yield of 82%.

The element analysis of the complex A16 was performed, and it had the molecular formula of $C_{14}H_{12}ZnO_2$ and the molecular weight of 277.63: C, 60.57; H, 4.36; O, 11.53; Zn, 23.55.

The production methods of complexes A17-A19 were same with that of A16, except that ethanol, isopropanol, n-butanol, and t-butanol were used in this order to obtain complexes A20-A22, respectively.

The element analysis of the resultant complexes A17-A19 was performed. The complex A20 had the molecular formula of $C_2H_6ZnO_2$ and the molecular weight of 127.46: C, 18.85; H, 4.74; O, 25.11; Zn, 51.30.

The complex A17 had the molecular formula of $C_4H_{10}ZnO_2$ and the molecular weight of 155.51: C, 30.89; H, 6.48; O, 20.58; Zn, 42.05.

The complex A18 had the molecular formula of $C_6H_{14}ZnO_2$ and the molecular weight of 183.56: C, 39.26; H, 7.69; O, 17.43; Zn, 35.62.

The complex A19 had the molecular formula of $C_8H_{18}ZnO_2$ and the molecular weight of 211.62: C, 45.41; H, 8.57; O, 15.12; Zn, 30.90.

Example 6

Production of Metal Alkoxide Complex A20

Under a water-free and oxygen-free condition, 10 mL of a tetrahydrofuran solution containing diphenylcarbinol was added to a tetrahydrofuran solution containing titanium tetrachloride slowly and dropwise, wherein the content of the diphenylcarbinol was 0.72 g (4 mmol), and the content of the titanium tetrachloride was 0.19 g (1 mmol). The reaction of tetrahydrofuran was performed under reflux for 24 h, and then 0.002 g of elementary iodine was added, the reaction equation was as follows:

The resultant reaction mixture was cooled, and 0.80 g of the complex A20 was obtained as white solid after filtration with the yield of 89%.

The element analysis of the complex A20 was performed, and it had the molecular formula of $(C_{56}H_{52}O_4Ti)(THF)$ and the molecular weight of 908.98: C, 79.28; H, 6.65; O, 8.80; Ti, 5.27.

Example 7

Production of Metal Alkoxide Complex A21

Under a water-free and oxygen-free condition, 10 mL of a tetrahydrofuran solution containing triphenylcarbinol was added to a tetrahydrofuran solution containing dibutyl magnesium slowly and dropwise, wherein the content of the triphenylcarbinol was 0.52 g (2 mmol), and the content of the dibutyl magnesium of 1 ml (1 M heptane solution) (1 mmol). The reaction was performed at room temperature for 2 h, and the reaction equation was as follows:

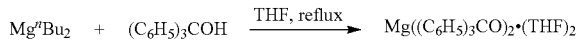

The resultant reaction mixture was cooled and concentrated, and 0.60 g of the complex A21 was obtained as white solid after filtration with the yield of 88%.

The element analysis of the complex A21 was performed, and it had the molecular formula of $C_{38}H_{30}MgO_3(THF)$ and the molecular weight of 687.16: C, 80.40; H, 6.75; Mg, 3.54; O, 9.31.

Example 8

At room temperature, 10 µmol of the complex A1 obtained in Example 1, 20 µmol of benzoic alcohol and 5 mL of toluene as a solvent were added into a 20 mL water-free and oxygen-free polymerization bottle (penicillin bottle, SYNTHWARE GLASS Co., Ltd.). After the reaction was performed at 20° C. for 5 minutes, 0.2 mmol ϵ-caprolactone monomer was added. The reaction was performed under agitation at room temperature for 5 minutes. A solution of 10 vol. % hydrochloric acid in ethanol was added to stop the reaction. The reaction solution was poured into a 150 ml vessel containing 100 ml ethanol so as to be sedimentated. A white solid was obtained by filtration. The white solid was dried in a 40° C. vacuum drying chamber until the weight is constant, thereby a poly-ϵ-caprolactone solid is obtained. The conversion measure by a nuclear magnetic resonance test was 100%. As analyzed by a gel permeation chromatography (GPC), the molecular weight $M_n$ of the poly-ϵ-caprolactone is 2200, and $M_w/M_n=1.21$.

Example 9

At room temperature, 10 µmol of the complex A1 obtained in Example 1, 20 µmol of benzoic alcohol and 5 mL of toluene solvent were added into a 15 mL water-free and oxygen-free polymerization bottle. After the reaction was performed at 20° C. for 5 minutes, a catalyst composition was formed. Then 40 mmol of L-lactide monomer was added and the mixture was stirred at room temperature to react for 15 minutes. A solution of 10 vol. % hydrochloric acid in ethanol was added to stop the reaction. The reaction solution was poured into ethanol so as to be sedimentated. A white solid was obtained by filtration. The white solid was dried in a 40° C. vacuum drying chamber for 48 h to obtain poly-L-lactide solid. The conversion measured by a nuclear magnetic resonance test was 98%. As analyzed by GPC, the molecular weight $M_n$ of the poly-L-lactide is 6100, and $M_w/M_n=1.25$.

Example 10

At room temperature, 10 µmol of the complex A2 obtained in Example 1, 1 mmol of isopropanol and 15 mL of toluene solvent were added into a 25 mL water-free and oxygen-free polymerization bottle. After the reaction was performed at 20° C. for 5 minutes, a catalyst composition was formed. Then 20 mmol of ϵ-caprolactone monomer was added and the mixture was stirred at room temperature to react for 3 h. A solution of 10 vol. % hydrochloric acid in ethanol was added to stop the reaction. The reaction solution was poured into ethanol so as to be sedimentated. A white solid was obtained by filtration. The solid was placed in a vacuum drying chamber, and dried at 40° C. for 48 h to obtain poly-ϵ-caprolactone having a net weight of 2.28 g. The conversion measured by a nuclear magnetic resonance test was 99%. As analyzed by GPC, the molecular weight $M_n$ of the poly-ϵ-caprolactone is 1100, and $M_w/M_n=1.09$.

Example 11

At room temperature, a solution of 10 µmol of the complex A2 obtained in Example 1 dissolved in 10 ml of tetrahydrofuran were added into a 25 mL water-free and oxygen-free polymerization bottle. 20 mmol of L-lactide monomer was added and the mixture was stirred at room temperature to react for 3 h. A mixture solution of 5 vol. % water and ethanol was added to stop the reaction. The reaction solution was poured into ethanol so as to be sedimentated. A white solid was obtained by filtration. The solid was placed in a vacuum drying chamber, and dried at 40° C. for 48 h to obtain poly-L-lactide having a net weight of 2.82 g. The conversion measured by a nuclear magnetic resonance test was 98%. As analyzed by GPC, the molecular weight $M_n$ of the poly-L-lactide is 1500, and $M_w/M_n=1.08$.

Example 12

At room temperature, 10 µmol of the complex A3 obtained in Example 1, 20 µmol of diphenylcarbinol and 15 mL of toluene solvent were added into a 25 mL water-free and oxygen-free polymerization bottle. After the reaction was performed at 20° C. for 5 minutes, a catalyst composition was obtained. Then 50 mmol of ϵ-caprolactone monomer was added and the mixture was stirred at room temperature to react for 3 h. A solution of 10 vol. % hydrochloric acid in ethanol was added to stop the reaction. The reaction solution was poured into ethanol so as to be sedimentated. A white solid was obtained by filtration. The solid was placed in a vacuum drying chamber, and dried at 40° C. for 48 h to obtain poly-ϵ-caprolactone having a net weight of 2.28 g. The conversion measured by a nuclear magnetic resonance test was 100%. As analyzed by GPC, the molecular weight $M_n$ of the poly-ε-caprolactone is 601,000, and $M_w/M_n=1.20$.

Example 13

At room temperature, 10 μmol of the complex A3 obtained in Example 1, 20 μmol of diphenylcarbinol and 40 mL of toluene solvent were added into a 100 mL water-free and oxygen-free polymerization bottle. After the reaction was performed at 20° C. for 5 minutes, a catalyst composition was obtained. Then 10 mmol of L-lactide monomer was added and the mixture was stirred at room temperature to react for 5 h. A solution of 10 vol. % hydrochloric acid in ethanol was added to stop the reaction. The reaction solution was poured into ethanol so as to be sedimentated. A white solid was obtained by filtration. The solid was placed in a vacuum drying chamber, and dried at 40° C. for 48 h to obtain poly-L-lactide having a net weight of 2.82 g. The conversion measured by a nuclear magnetic resonance test was 98%. As analyzed by GPC, the molecular weight $M_n$ of the poly-L-lactide is 81,000, and $M_w/M_n=1.03$.

Example 14

At room temperature, 10 μmol of the complex A4 obtained in Example 1, 60 μmol of benzoic alcohol and 30 mL of toluene solvent were added into a 50 mL water-free and oxygen-free polymerization bottle. After the reaction was performed at 20° C. for 5 minutes, 60 mmol of ε-caprolactone monomer were added and the mixture was stirred at room temperature to react for 2 h. A solution of 10 vol. % hydrochloric acid in ethanol was added to stop the reaction. The reaction solution was poured into ethanol so as to be sedimentated. A white solid was obtained by filtration. The solid was placed in a vacuum drying chamber, and dried at 40° C. for 48 h to obtain poly-ε-caprolactone having a net weight of 6.85 g. The conversion measured by a nuclear magnetic resonance test was 100%. As analyzed by GPC, the molecular weight $M_n$ of the poly-ε-caprolactone is 120,000, and $M_w/M_n=1.11$.

Example 15

At room temperature, 10 μmol of a solution of the complex A4 obtained in Example 1 in tetrahydrofuran solvent was added into a 100 mL water-free and oxygen-free polymerization bottle. Then 60 mmol of L-lactide monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 8.46 g. The conversion measured by a nuclear magnetic resonance test was 98%. As analyzed by GPC, the molecular weight $M_n$ of the poly-L-lactide is 662,000, and $M_w/M_n=1.48$.

Example 16

At room temperature, 10 μmol of the complex A5 obtained in Example 1, 10 mmol of isopropanol and 20 mL of toluene solvent were added into a 50 mL water-free and oxygen-free polymerization bottle. After the reaction was performed at 70° C. for 5 minutes, a catalyst composition was formed. Then 100 mmol of ε-caprolactone monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 11.3 g. The conversion measured by a nuclear magnetic resonance test was 99%. As analyzed by GPC, the molecular weight $M_n$ of the poly-ε-caprolactone is 1200, and $M_w/M_n=1.09$.

Example 17

At room temperature, 10 μmol of the complex A5 obtained in Example 1, 20 μmol of isopropanol and 20 mL of toluene solvent were added into a 50 mL water-free and oxygen-free polymerization bottle. After the reaction was performed at 70° C. for 5 minutes, a catalyst composition was formed. Then 30 mmol of L-lactide monomer was added and the mixture was stirred at room temperature to react for 1.67 h. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 4.28 g. The conversion measured by a nuclear magnetic resonance test was 99%. As analyzed by GPC, the molecular weight $M_n$ of the poly-L-lactide is 220,000, and $M_w/M_n=1.10$.

Example 18

At room temperature, 10 μmol of the complex A6 obtained in Example 1, 10 μmol of diphenylcarbinol and 30 mL of toluene solvent were added into a 50 mL water-free and oxygen-free polymerization bottle. After the reaction was performed at 70° C. for 5 minutes, a composition of catalyst was formed. Then 50 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. It was placed in a vacuum drying chamber, and dried at 40° C. for 48 h to obtain poly-ε-caprolactone having a net weight of 5.70 g. The conversion measured by a nuclear magnetic resonance test was 100%. As analyzed by GPC, the molecular weight $M_n$ of the poly-ε-caprolactone is 570,000, and $M_w/M_n=1.10$.

Example 19

At room temperature, 10 μmol of the complex A6 obtained in Example 1, 5 μmol of diphenylcarbinol and 10 mL of toluene solvent were added into a 25 mL water-free and oxygen-free polymerization bottle. After the reaction was performed at 70° C. for 5 minutes, a composition of catalyst was formed. Then 20 mmol of L-lactide monomer was added and the mixture was stirred at room temperature to react for 40 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 300,000, and $M_w/M_n=1.09$.

Example 20

At room temperature, 10 μmol of the complex A7 obtained in Example 1, 20 μmol of isopropanol and 50 mL of toluene solvent were added into a 100 mL water-free and oxygen-free polymerization bottle. After the reaction was performed at 70° C. for 5 minutes, a composition of catalyst was formed. Then 100 mmol of ε-caprolactone monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 19.0 g. The conversion measured by a nuclear magnetic resonance test was 80%. As analyzed by GPC, the molecular weight $M_n$ of the poly-ε-caprolactone is 590,000, and $M_w/M_n=1.31$.

Example 21

At room temperature, 10 μmol of the complex A7 obtained in Example 2, 20 mol of isopropanol and 10 mL of toluene solvent were added into 25 mL water-free and oxygen-free polymerization bottle. After the reaction was performed at 70° C. for 5 minutes, 50 mol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 340,000, and $M_w/M_n=1.14$.

Example 22

At room temperature, 10 μmol of the complex A8 obtained in Example 2, 20 μmol of benzoic alcohol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 5% water and ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 139,000, and $M_w/M_n=1.07$.

Example 23

At room temperature, 10 μmol of the complex A8 obtained in Example 1, 20 μmol of benzoic alcohol and 10 mL of toluene solvent were added into a 25 mL water-free and oxygen-free polymerization bottle. After the reaction was performed at 20° C. for 5 minutes, a composition of catalyst was formed. Then 20 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.88 g. The conversion measured by a nuclear magnetic resonance test was 100%. As analyzed by GPC, the molecular weight $M_n$ of the poly-L-lactide is 164,000, and $M_w/M_n=1.09$.

Example 24

At room temperature, 10 μmol of the complex A9 obtained in Example 2, 20 μmol of diphenylcarbinol and 10 mL of toluene solvent were added into a 25 mL water-fee and oxygen-free polymerization bottle. After the reaction was performed at 70° C. for 5 minutes, a catalyst composition was formed. Then 50 mmol of L-lactide monomer was added and the mixture was stirred at room temperature to react for 0.5 h. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 340,000, and $M_w/M_n=1.14$.

Example 25

At room temperature, 10 μmol of the complex A9 obtained in Example 2, 10 μmol of diphenylcarbinol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 256,000, and $M_w/M_n=1.27$.

Example 26

At room temperature, 10 μmol of the complex A10 obtained in Example 3, 20 μmol of isopropanol and 50 mL of toluene solvent were added into a 100 mL water-free and oxygen-free polymerization bottle. After the reaction was performed at 70° C. for 5 minutes, a catalyst composition was formed. Then 100 mmol of ε-caprolactone monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 19.0 g. The conversion measured by a nuclear magnetic resonance test was 80%. As analyzed by GPC, the molecular weight $M_n$ of the poly-ε-caprolactone is 510,000, and $M_w/M_n$=1.30.

Example 27

At room temperature, 10 μmol of the complex A10 obtained in Example 3, 20 μmol of isopropanol and 10 mL of toluene solvent were added into a 25 mL water-free and oxygen-free polymerization bottle. After the reaction was performed at 70° C. for 5 minutes, a catalyst composition was formed. Then 50 mmol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 346,000, and $M_w/M_n$=1.24.

Example 28

At room temperature, 10 μmol of the complex A11 obtained in Example 3, 5μmol of diphenylcarbinol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 510,000, and $M_w/M_n$=1.37.

Example 29

At room temperature, 10 μmol of the complex A11 obtained in Example 3, 20 μmol of diphenylcarbinol and 10 mL of toluene solvent were added into a 25 mL water-free and oxygen-free polymerization bottle. After the reaction was performed at 20° C. for 5 minutes, a catalyst composition was formed. Then 20 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.88 g. The conversion measured by a nuclear magnetic resonance test was 100%. As analyzed by GPC, the molecular weight $M_n$ of the poly-L-lactide is 164,000, and $M_w/M_n$=1.09.

Example 30

At room temperature, 10 μmol of the complex A12 obtained in Example 3, 20 μmol of diphenylcarbinol and 10 mL of toluene solvent were added into a 25 mL water-free and oxygen-free polymerization bottle. After the reaction was performed at 70° C. for 5 minutes, a catalyst composition was formed. Then 50 mmol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 340,000, and $M_w/M_n$=1.14.

Example 31

At room temperature, 10 μmol of the complex A12 obtained in Example 3, 10 μmol of diphenylcarbinol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 278,000, and $M_w/M_n$=1.17.

Example 32

At room temperature, 10 μmol of the complex A13 obtained in Example 3, 50 μmol of isopropanol and 50 mL of toluene solvent were added into a 100 mL water-free and oxygen-free polymerization bottle. After the reaction was performed at 70° C. for 5 minutes, a catalyst composition was formed. Then 100 mmol of ε-caprolactone monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 19.0 g. The conversion measured by a nuclear magnetic resonance test was 80%. As analyzed by GPC, the molecular weight $M_n$ of the poly-ε-caprolactone is 250,000, and $M_w/M_n$=1.09.

Example 33

At room temperature, 10 μmol of the complex A13 obtained in Example 3, 20 μmol of isopropanol and 10 mL of toluene solvent were added into a 25 mL water-free and oxygen-free polymerization bottle. After the reaction was performed at 70° C. for 5 minutes, a catalyst composition was formed. Then 50 mmol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight $M_n$ of the poly-L-lactide is 360,000, and $M_w/M_n=1.14$.

Example 34

At room temperature, 10 μmol of the complex A14 obtained in Example 3, 20 μmol of benzoic alcohol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 139,000, and $M_w/M_n=1.17$.

Example 35

At room temperature, 10 μmol of the complex A14 obtained in Example 2, 20 μmol of benzoic alcohol and 10 mL of toluene solvent were added into a 25 mL water-free and oxygen-free polymerization bottle. After the reaction was performed at 20° C. for 5 minutes, a catalyst composition was formed. Then 20 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. As white poly-L-lactide solid was obtained by filtration. The solid was placed in a vacuum drying chamber, and dried at 40° C. for 48 h to obtain poly-L-lactide having a net weight of 2.88 g. The conversion measured by a nuclear magnetic resonance test was 100%. As analyzed by GPC, the molecular weight $M_n$ of the poly-L-lactide $M_n=16,400$, and $M_w/M_n=1.09$.

Example 36

At room temperature, 10 μmol of the complex A15 obtained in Example 4, 20 μmol of diphenylcarbinol and 10 mL of toluene solvent were added into a 25 mL water-free and oxygen-free polymerization bottle. After the reaction was performed at 70° C. for 5 minutes, a catalyst composition was formed. Then 50 mmol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide monomer was added and the filtration. The solid was placed in a vacuum drying chamber, and dried at 40° C. for 48 h to obtain poly-L-lactide having a net weight of 2.85 g. The conversion measured by a nuclear magnetic resonance test was 99%. As analyzed by GPC, the molecular weight of the poly-L-lactide $M_n=38,0000$, and $M_w/M_n=1.14$.

Example 37

At room temperature, 10 μmol of the complex A15 obtained in Example 4, 0.2 mmol of diphenylcarbinol and 10 mL of toluene solvent were added into a 25 mL water-free and oxygen-free polymerization bottle. After the reaction was performed at 20° C. for 5 minutes, a catalyst composition was formed. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 115,000, and $M_w/M_n=1.07$.

Example 38

At room temperature, 10 μmol of the complex A16 obtained in Example 5, 20 μmol of isopropanol and 50 mL of toluene solvent were added into a 100 mL water-free and oxygen-free polymerization bottle. After the reaction performed at 70° C. for 5 minutes, a catalyst composition was formed. Then 100 mmol of ε-caprolactone monomer was added and the mixture was stirred at room temperature to react for 1 h. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 10.0 g. The conversion measured by a nuclear magnetic resonance test was 88%. As analyzed by GPC, the molecular weight $M_n$ of the poly-ε-caprolactone is 590,000, and $M_w/M_n=1.31$.

Example 39

At room temperature, 10 μmol of the complex A16 obtained in Example 5, 20 μmol of isopropanol and 10 mL of toluene solvent were added into a 25 mL water-free and oxygen-free polymerization bottle. After the reaction was performed at 70° C. for 5 minutes, a catalyst composition was formed. Then 50 mmol of L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 7.13 g. The conversion measured by a nuclear magnetic resonance test was 99%. As analyzed by GPC, the molecular weight $M_n$ of the poly-L-lactide is 340,000, and $M_w/M_n=1.14$.

Example 40

At room temperature, 10 μmol of the complex A17 obtained in Example 5, 30 μmol of benzoic alcohol and 10 mL of toluene solvent were added into a 25 mL water-free and oxygen-free polymerization bottle. After the reaction was performed at 20° C. for 5 minutes, a catalyst composition was formed. Then 30 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 3.42 g. The conversion measured by a nuclear magnetic resonance test was 100%. As analyzed by GPC, the molecular weight $M_n$ of the poly-ε-caprolactone is 136,000, and $M_w/M_n=1.17$.

Example 41

At room temperature, 10 μmol of the complex A17 obtained in Example 5, 30 μmol of benzoic alcohol and 10 mL of dichloromethane solvent were added into a 25 mL water-free and oxygen-free polymerization bottle. After the reaction was performed at 20° C. for 5 minutes, 30 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 4.32 g. The conversion measured by a nuclear magnetic resonance test was 100%. As analyzed by GPC, the molecular weight $M_n$ of the poly-L-lactide is 168,000, and $M_w/M_n=1.09$.

Example 42

At room temperature, 10 μmol of the complex A18 was obtained in Example 5, 20 μmol of methanol and 10 mL of tetrahydrofuran solvent were added into a 25 mL water-free and oxygen-free polymerization bottle. After the reaction was performed at 20° C. for 5 minutes, a catalyst composition was obtained. Then 3 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 0.43 g. The conversion measure by a nuclear magnetic resonance test was 100%. As analyzed by GPC, the molecular weight $M_n$ of the poly-L-lactide is 138,000, and $M_w/M_n=1.09$.

Example 43

At room temperature, 10 μmol of the complex A18 obtained in Example 5, 30 μmol of ethanol and 10 mL of ethylene glycol solvent were added into a 25 mL water-free and oxygen-free polymerization bottle. After the reaction was performed at 20° C. for 5 minutes, a catalyst composition was obtained. Then 6 mmol of ε-caprolactone monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 0.68 g. The conversion measured by a nuclear magnetic resonance test was 100%. As analyzed by GPC, the molecular weight $M_n$ of the poly-ε-caprolactone is 240,000, and $M_w/M_n=1.15$.

Example 44

At room temperature, 10 μmol of the complex A19 obtained in Example 5, 30 μmol of n-butanol and 10 mL of tetrahydrofuran solvent were added into a 25 mL water-free and oxygen-free polymerization bottle. After the reaction was performed at 20° C. for 5 minutes, a catalyst composition was obtained. Then 6 mmol of L-lactide monomer was added and the mixture was stirred at room temperature to react for 10 minutes. A mixture solution of 5 vol. % water and ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 0.86 g. The conversion measure by a nuclear magnetic resonance test was 100%. As analyzed by GPC, the molecular weight $M_n$ of the poly-L-lactide is 299,000, and $M_w/M_n=1.18$.

Example 45

At room temperature, 10 μmol of the complex A19 obtained in Example 5 was added into a 25 mL water-free and oxygen-free polymerization bottle. Then 10 mL of tetrahydrofuran solvent was added. 50 mmol of ε-caprolactone monomer was added under powerful agitation and the mixture was stirred at room temperature to react for 10 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 5.71 g. The conversion measured by a nuclear magnetic resonance test was 100%. As analyzed by GPC, the molecular weight $M_n$ of the poly-ε-caprolactone is 600,000, and $M_w/M_n=1.49$.

Example 46

At room temperature, 10 μmol of the complex A20 obtained in Example 6, 20 μmol of diphenylcarbinol and 10 mL of tetrahydrofuran solvent were added into a 25 mL water-free and oxygen-free polymerization bottle. After the reaction was performed at 20° C. for 5 minutes, a catalyst composition was obtained. Then 12 mmol of ε-caprolactone monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 1.36 g. The conversion measured by a nuclear magnetic resonance test was 100%. As analyzed by GPC, the molecular weight $M_n$ of the poly-ε-caprolactone is 500,000, and $M_w/M_n=1.19$.

Example 47

At room temperature, 10 μmol of the complex A20 obtained in Example 6, 20 μmol of benzoic alcohol and 10 mL of toluene solvent were added into a 25 mL water-free and oxygen-free polymerization bottle. After the reaction was performed at 20° C. for 5 minutes, a catalyst composition was formed. The 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 140,000, and $M_w/M_n=1.09$.

Example 48

At room temperature, 10 μmol of the complex A20 obtained in Example 6 was added into a 25 mL water-free and oxygen-free polymerization bottle. 15 mL of hexane solvent was added. After the reaction was performed at 20° C. for 5 minutes, a catalyst composition was formed. Then 3 mmol of ε-caprolactone monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 3.42 g. The conversion measured by a nuclear magnetic resonance test was 100%. As analyzed by GPC, the molecular weight $M_n$ of the poly-ε-caprolactone is 343,000, and $M_w/M_n=1.29$.

Example 49

At room temperature, 10 μmol of the complex A20 obtained in Example 6, 20 μmol of benzoic alcohol and 10 mL of toluene solvent were added into a 25 mL water-free and oxygen-free polymerization bottle. After the reaction was performed at 20° C. for 60 minutes, a catalyst composition was formed. Then 20 mmol of L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 2.88 g. The conversion measured by a nuclear magnetic resonance test was 100%. As analyzed by GPC, the molecular weight $M_n$ of the poly-L-lactide is 170,000, and $M_w/M_n=1.19$.

Example 50

At room temperature, 10 μmol of the complex A21 obtained in Example 7, 20 μmol of diphenylcarbinol and 10 mL of toluene solvent were added into a 25 mL water-free and oxygen-free polymerization bottle. After the reaction was performed at 70° C. for 5 minutes, a catalyst composition was formed. Then 50 mmol L-lactide monomer was added and the mixture was stirred at room temperature to react for 30 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 7.21 g. The conversion measured by a nuclear magnetic resonance test was 99%. As analyzed by GPC, the molecular weight $M_n$ of the poly-L-lactide is 340,000, and $M_w/M_n=1.14$.

Example 51

At room temperature, 10 μmol of the complex A21 obtained in Example 7, 20 μmol of diphenylcarbinol and 10 mL of toluene solvent were added into a 25 mL water-free and oxygen-free polymerization bottle. After the reaction was performed at 20° C. for 5 minutes, a catalyst composition was obtained. Then 20 mmol of ε-caprolactone monomer was added and the mixture was stirred at room temperature to react for 20 minutes. A solution of 10 vol. % hydrochloric acid in ethanol was added to stop the reaction. The reaction solution was poured into ethanol so as to be sedimentated. A white poly-ε-caprolactone solid was obtained by filtration. The solid was placed in a vacuum drying chamber, and dried at 40° C. for 48 h to obtain poly-ε-caprolactone having a net weight of 2.28 g. The conversion measured by a nuclear magnetic resonance test was 100%. As analyzed by GPC, the molecular weight $M_n$ of the poly-ε-caprolactone is 139,000, and $M_w/M_n=1.07$.

Example 52

At room temperature, 10 μmmol of the complex A17 obtained in Example 5 and 10 mL of toluene solvent were added into a 25 mL water-free and oxygen-free polymerization bottle. Then 10 mmol of ε-caprolactone monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-ε-caprolactone solid was obtained by filtration. It was placed in a vacuum drying chamber, and dried at 40° C. for 48 h. The net weight thereof was 1.14 g. The conversion measured by a nuclear magnetic resonance test was 100%. As analyzed by GPC, the molecular weight $M_n$ of the poly-ε-caprolactone is 118,000 and $M_w/M_n=1.47$.

Example 53

At room temperature, a toluene solution of 10 μmold of the complex A17 obtained in Example 5 was added into a 25 mL water-free and oxygen-free polymerization bottle. Then 10 mmol L-lactide monomer was added and the mixture was stirred at room temperature to react for 10 minutes. A solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 1.44 g. The conversion measure by a nuclear magnetic resonance test was 100%. As analyzed by GPC, the molecular weight $M_n$ of the poly-L-lactide is 159,000, and $M_w/M_n=1.37$.

Example 54

At 130° C., 2.5 mol of L-lactide monomer and 25 mmol of the complex A17 obtained in Example 5 were mixed, melted and polymerized. After the reaction was performed for 20 minutes, a solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 3.31 g. The conversion measure by a nuclear magnetic resonance test was 92%. As analyzed by GPC, the molecular weight $M_n$ of the poly-L-lactide is 134,000, and $M_w/M_n=1.33$.

Example 55

At 130° C., 25 mol of L-lactide monomer, 12.5 mmol of the complex A17 obtained in Example 5 and 25 mmol of benzoic alcohol were mixed, melted and polymerized. After the reaction was performed for 10 minutes, a solution of 10 vol. % hydrochloric acid in ethanol was added to stop the reaction. The reaction solution was poured into ethanol so as to be sedimentated. A white poly-L-lactide solid was obtained by filtration. The solid was placed in a vacuum drying chamber, and dried at 40° C. for 48 h to obtain poly-L-lactide having a net weight of 3.3 kg. The conversion measure by a nuclear magnetic resonance test was 92%. As analyzed by GPC, the molecular weight $M_n$ of the poly-L-lactide is 134,000, and $M_w/M_n=1.35$.

Example 56

At 130° C., 25 mol of L-lactide monomer, 12.5 mmol of the complex A17 obtained in Example 5 and 25 mmol of benzoic alcohol were mixed, melted and polymerized. After the reaction was performed for 10 minutes, a catalyst compositions was obtained. A mixture solution of 20 vol. % water and ethanol was added to stop the reaction. The reaction solution was poured into ethanol so as to be sedimentated. A white poly-L-lactide solid was obtained by filtration. The solid was placed in a vacuum drying chamber, and dried at 50° C. for 30 h to obtain poly-L-lactide having a net weight of 3.3 kg. The conversion measured by a nuclear magnetic resonance test was 92%. As analyzed by GPC, the molecular weight $M_n$ of the poly-L-lactide is 134,000, and $M_w/M_n=1.35$.

Example 57

By using the method of the following Example 52, poly-ε-caprolactone was synthesized by adopting different mixtures of benzoic alcohol and the complex A17, respectively, wherein all the molar ratios of the ε-caprolactone monomer to the complex A17 were 5000:1, and the molar ratios of benzoic alcohol to the complex A17 were listed in Table 1. The molecular weight and molecular weight distribution of the products poly-ε-caprolactone were listed in Table 1.

TABLE 1

The ratios of alcohols to the complex A17; and molecular weight and molecular weight distribution of poly-ε-caprolactone

| Ratios of alcohols to the complex A17 | $M_{n,calcd} \times 10^{-4}$ | $M_{n,GPC} \times 10^{-4}$ | PDI |
|---|---|---|---|
| 2:1 | 5.72 | 5.88 | 1.10 |
| 3:1 | 3.82 | 3.69 | 1.09 |
| 5:1 | 2.29 | 2.22 | 1.04 |
| 7:1 | 1.64 | 1.60 | 1.06 |
| 9:1 | 1.28 | 1.30 | 1.08 |
| 11:1 | 1.05 | 1.10 | 1.03 |
| 14:1 | 0.83 | 0.98 | 1.01 |

In Table 1, $M_{n,calcd}$ is the calculated molecular weight of poly-ε-caprolactone; $M_{n,GPC}$ is the molecular weight of poly-ε-caprolactone measured by the gel permeation chromatography; and PDI is the dispersion index of poly-ε-caprolactone.

Example 58

By suing the method of Example 53, poly-L-lactide was synthesized by adopting different mixtures of benzoic alcohol and the complex A17 respectively, wherein all the molar ratios of the poly-L-lactide monomers to the complex A17 were 1000: 1, and the molar ratios of benzoic alcohol to the complex A17 were listed in Table 1. The molecular weights and molecular weight distributions of the products poly-L-lactide were listed in Table 2.

TABLE 2

The ratios of alcohols to the complex A17; and molecular weight and molecular weight distribution of poly-L-lactide

| Ratios of alcohols to the complex A17 | $M_{n,calcd} \times 10^{-4}$ | $M_{n,GPC} \times 10^{-4}$ | PDI |
|---|---|---|---|
| 2:1 | 7.22 | 7.30 | 1.03 |
| 3:1 | 4.82 | 4.98 | 1.05 |
| 5:1 | 2.89 | 2.80 | 1.08 |
| 7:1 | 2.07 | 2.00 | 1.04 |
| 9:1 | 1.61 | 1.70 | 1.07 |
| 10:1 | 1.45 | 1.44 | 1.08 |
| 12:1 | 1.22 | 1.30 | 1.05 |

In Table 2, $M_{n,calcd}$ is the calculated molecular weight of poly-L-lactide; $M_{n,GPC}$ is the molecular weight of poly-L-lactide measured by the gel permeation chromatography; and PDI is the dispersion index of poly-L-lactide.

The Examples above are only used to help the understanding of the invention and the inventive idea thereof. It should be recognized that those skilled in the art can make some changes and modifications to the invention without depart from the principle of the invention. Such changes and modifications also fall within the protection scope of the claims of the invention.

The invention claimed is:

1. A catalyst composition, comprising a metal alkoxide complex and a hydroxy-containing compound, wherein the molar ratio of the metal alkoxide complex to the hydroxy-containing compound is in a range of 1:2-1:1,000, and wherein the metal alkoxide complex has a molecular formula represented by Formula (I):

$$[X_{0-2}M(OCR^1R^2R^3)_{1-3}]_{1-6}\cdot(\text{organic solvent})_{0-4} \qquad (I);$$

wherein in Formula (I), M is calcium, magnesium, strontium, barium, or aluminium;

wherein $R^1$, $R^2$, and $R^3$ are independently selected from hydrogen, chain alkyl, phenyl, substituted phenyl, arylalkyl, or substituted arylalkyl, and wherein if one of R¹, R², and R³ is hydrogen or chain alkyl, at least one of the other two substituents is phenyl, substituted phenyl, arylalkyl, or substituted arylalkyl;

X is hydrogen, $C_1$-$C_{30}$ chain alkyl, amino, or halogen.

2. The catalyst composition according to claim 1, wherein the hydroxy-containing compound is ethylene glycol, benzoic alcohol, phenethanol, diphenylcarbinol, triphenylcarbinol, 1,1,1-triphenylethanol, 9-anthracenemethanol, 1,3,5-benzenetriol, triethanolamine, or 1,3,5-benzenetrimethanol.

3. The catalyst composition according to claim 1, wherein M is magnesium or aluminum.

4. The catalyst composition according to claim 1, wherein R¹, R², and R³ independently are hydrogen, methyl, phenyl, substituted phenyl, arylalkyl, or substituted arylalkyl, and wherein if one of R¹, R², and R³ is hydrogen or methyl, at least one of the other two groups is phenyl, substituted phenyl, arylalkyl, or substituted arylalkyl.

5. The catalyst composition according to claim 1, wherein when M is magnesium, X is H, $CH_3$, $CH_2CH_3$, $CH_2Si(CH_3)_3$, $N(Si(CH_3)_3)_2$, benzyl, substituted benzyl, or halogen; and wherein when M is calcium, X is H, $CH_3$, $CH_2CH_3$, $CH_2CH_2CH_2CH_3$, $CH_2Si(CH_3)_3$, $N(Si(CH_3)_3)_2$, benzyl, substituted benzyl, or halogen.

6. The catalyst composition according to claim 1, wherein the organic solvent is alkanes, substituted alkanes, benzene, substituted benzene, or ethers.

7. A production method of poly-ε-caprolactone or polylactide comprising the following steps:
reacting an ε-caprolactone monomer or a lactide monomer in the presence of a catalyst to obtain poly-ε-caprolactone or polylactide, wherein the catalyst is a metal alkoxide complex having a molecular formula represented by Formula (I):

$[X_{0-2}M(OCR^1R^2R^3)_{1-3}]_{1-6} \cdot (\text{organic solvent})_{0-4}$    (I);

wherein in Formula (I), M is calcium, magnesium, strontium, barium, or aluminium;
wherein R¹, R², and R³ are independently selected from hydrogen, chain alkyl, phenyl, substituted phenyl, arylalkyl, or substituted arylalkyl, and wherein if one of R¹, R², and R³ is hydrogen or chain alkyl, at least one of the other two substituents is phenyl, substituted phenyl, arylalkyl, or substituted arylalkyl;

X is hydrogen, $C_1$-$C_{30}$ chain alkyl, amino, or halogen.

8. The production method according to claim 7, wherein the molar ratio of the metal alkoxide complex to the ε-caprolactone monomer or the lactide monomer is in the range of 1:1-1:10,000.

9. The production method according to claim 7, wherein the reaction temperature is 10° C.-130° C., and the reaction time is 0.03 h-24 h.

10. The production method according to claim 7, wherein M is magnesium or aluminum.

11. The production method according to claim 7, wherein R¹, R², and R³ independently are hydrogen, methyl, phenyl, substituted phenyl, arylalkyl, or substituted arylalkyl, and wherein if one of R¹, R², and R³ is hydrogen or methyl, at least one of the other two groups is phenyl, substituted phenyl, arylalkyl, or substituted arylalkyl.

12. The production method according to claim 7, wherein when M is magnesium, X is H, $CH_3$, $CH_2CH_3$, $CH_2Si(CH_3)_3$, $N(Si(CH_3)_3)_2$, benzyl, substituted benzyl, or halogen; and wherein when M is calcium, X is H, $CH_3$, $CH_2CH_3$, $CH_2CH_2CH_2CH_3$, $CH_2Si(CH_3)_3$, $N(Si(CH_3)_3)_2$, benzyl, substituted benzyl, or halogen.

13. The production method according to claim 7, wherein the organic solvent is alkanes, substituted alkanes, benzene, substituted benzene, or ethers.

* * * * *